(12) United States Patent
Park

(10) Patent No.: US 11,253,706 B2
(45) Date of Patent: Feb. 22, 2022

(54) SYSTEMS AND METHODS FOR CONTACT SELECTION IN DEEP BRAIN STIMULATION

(71) Applicant: ADVANCED NEUROMODULATION SYSTEMS, INC., Plano, TX (US)

(72) Inventor: Hyun-Joo Park, Frisco, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 250 days.

(21) Appl. No.: 16/703,176

(22) Filed: Dec. 4, 2019

(65) Prior Publication Data

US 2020/0269053 A1 Aug. 27, 2020

Related U.S. Application Data

(60) Provisional application No. 62/811,435, filed on Feb. 27, 2019.

(51) Int. Cl.
*A61B 34/10* (2016.01)
*A61N 1/36* (2006.01)
*A61B 5/00* (2006.01)
*A61N 1/05* (2006.01)

(52) U.S. Cl.
CPC ........ *A61N 1/36185* (2013.01); *A61B 5/4893* (2013.01); *A61B 34/10* (2016.02); *A61N 1/0534* (2013.01)

(58) Field of Classification Search
CPC ........... A61B 34/10; A61B 5/293; A61B 5/37; A61B 5/374; A61B 5/4836; A61B 5/4893; A61B 5/686; A61B 5/6868; A61B 5/725; A61N 1/0534; A61N 1/36139; A61N 1/36171; A61N 1/36185

See application file for complete search history.

(56) References Cited

U.S. PATENT DOCUMENTS

2018/0221091 A1* 8/2018 Piron ..................... A61B 34/00

* cited by examiner

*Primary Examiner* — George Manuel

(57) ABSTRACT

The present disclosure provides systems and methods for selecting contacts for use in deep brain stimulation (DBS). A computing device includes a processor and a memory device communicatively coupled to the processor. The memory device includes instructions that, when executed, cause the processor to apply a spatial filter to local field potential (LFP) recordings for a plurality of contacts of a DBS lead, calculate a power spectral density (PSD) for each contact from the filtered LFP for that contact, calculate a parametric approximation for each PSD, select at least one frequency band based on the parametric approximations, calculate a spectral coherency matrix for each of the at least one selected frequency band, and calculate an eigenvector centrality for each spectral coherency matrix to facilitate identifying a contact for stimulation.

20 Claims, 7 Drawing Sheets

SYSTEMS AND METHODS FOR CONTACT SELECTION IN DEEP BRAIN STIMULATION

CROSS REFERENCE TO RELATED APPLICATIONS

This application claims priority to provisional application Ser. No. 62/811,435, filed Feb. 27, 2019, which is incorporated herein in its entirety.

FIELD OF THE DISCLOSURE

The present disclosure relates generally to neurostimulation systems, and more particularly to selecting contacts for use in deep brain stimulation applications.

BACKGROUND ART

Deep brain stimulation (DBS) is an established neuromodulation therapy for the treatment of movement disorders, and has been shown to improve cardinal motor symptoms of Parkinson's Disease (PD), such as bradykinesia, rigidity, and tremors. DBS is also used to essential tremor (ET).

To maximize therapeutic effects of DBS, techniques may be implemented to select particular stimulation contacts for use in applying DBS. However, at least some known methods of selecting stimulation contacts are relatively time-consuming. Further, such methods may also be dependent on the behavioral outcome (e.g., tremor reduction) during a DBS programming session. Accordingly, it would be desirable to provide improved systems and methods for stimulation contact selection in DBS applications.

BRIEF SUMMARY OF THE DISCLOSURE

In one embodiment, the present disclosure is directed to a computing device for selecting contacts for use in deep brain stimulation (DBS). The computing device includes a processor and a memory device communicatively coupled to the processor. The memory device includes instructions that, when executed, cause the processor to apply a spatial filter to local field potential (LFP) recordings for a plurality of contacts of a DBS lead, calculate a power spectral density (PSD) for each contact from the filtered LFP for that contact, calculate a parametric approximation for each PSD, select at least one frequency band based on the parametric approximations, calculate a spectral coherency matrix for each of the at least one selected frequency band, and calculate an eigenvector centrality for each spectral coherency matrix to facilitate identifying a contact for stimulation.

In another embodiment, a computer-implemented method for selecting contacts for use in deep brain stimulation (DBS) is provided. The method includes applying a spatial filter to local field potential (LFP) recordings for a plurality of contacts of a DBS lead, calculating a power spectral density (PSD) for each contact from the filtered LFP for that contact, calculating a parametric approximation for each PSD, selecting at least one frequency band based on the parametric approximations, calculating a spectral coherency matrix for each of the at least one selected frequency band, and calculating an eigenvector centrality for each spectral coherency matrix to facilitate identifying a contact for stimulation.

In yet another embodiment, a system for deep brain stimulation (DBS) is provided. The system includes a DBS lead including a plurality of contacts, and a computing device communicatively coupled to the DBS lead. The computing device is configured to apply a spatial filter to local field potential (LFP) recordings for the plurality of contacts, calculate a power spectral density (PSD) for each contact from the filtered LFP for that contact, calculate a parametric approximation for each PSD, select at least one frequency band based on the parametric approximations, calculate a spectral coherency matrix for each of the at least one selected frequency band, and calculate an eigenvector centrality for each spectral coherency matrix to facilitate identifying a contact for stimulation.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides systems and methods for selecting contacts for use in deep brain stimulation (DBS). A spatial filter is applied to local field potential (LFP) recordings for a plurality of contacts of a DBS lead, and a power spectral density (PSD) is calculated for each contact from the filtered LFP for that contact. Further, a parametric approximation for each PSD is calculated, and at least one frequency band is selected based on the parametric approximations. For each of the at least one selected frequency band, a spectral coherency matrix is calculated, and an eigenvector centrality is calculated for each spectral coherency matrix to facilitate identifying a contact for stimulation.

Neurostimulation systems are devices that generate electrical pulses and deliver the pulses to nerve tissue of a patient to treat a variety of disorders. One category of neurostimulation systems is DBS. In DBS, electrical pulses are delivered to parts of a subject's brain, for example, for the treatment of movement and effective disorders such as PD and essential tremor.

Neurostimulation systems generally include a pulse generator and one or more leads. A stimulation lead includes a lead body of insulative material that encloses wire conductors. The distal end of the stimulation lead includes multiple electrodes, or contacts, that are electrically coupled to the wire conductors. The proximal end of the lead body includes multiple terminals (also electrically coupled to the wire conductors) that are adapted to receive electrical pulses. In DBS systems, the stimulation lead is implanted within the brain tissue to deliver the electrical pulses. The stimulation leads are then tunneled to another location within the patient's body to be electrically connected with a pulse generator or, alternatively, to an "extension." The pulse generator is typically implanted within a subcutaneous pocket created during the implantation procedure.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

Figure 1:
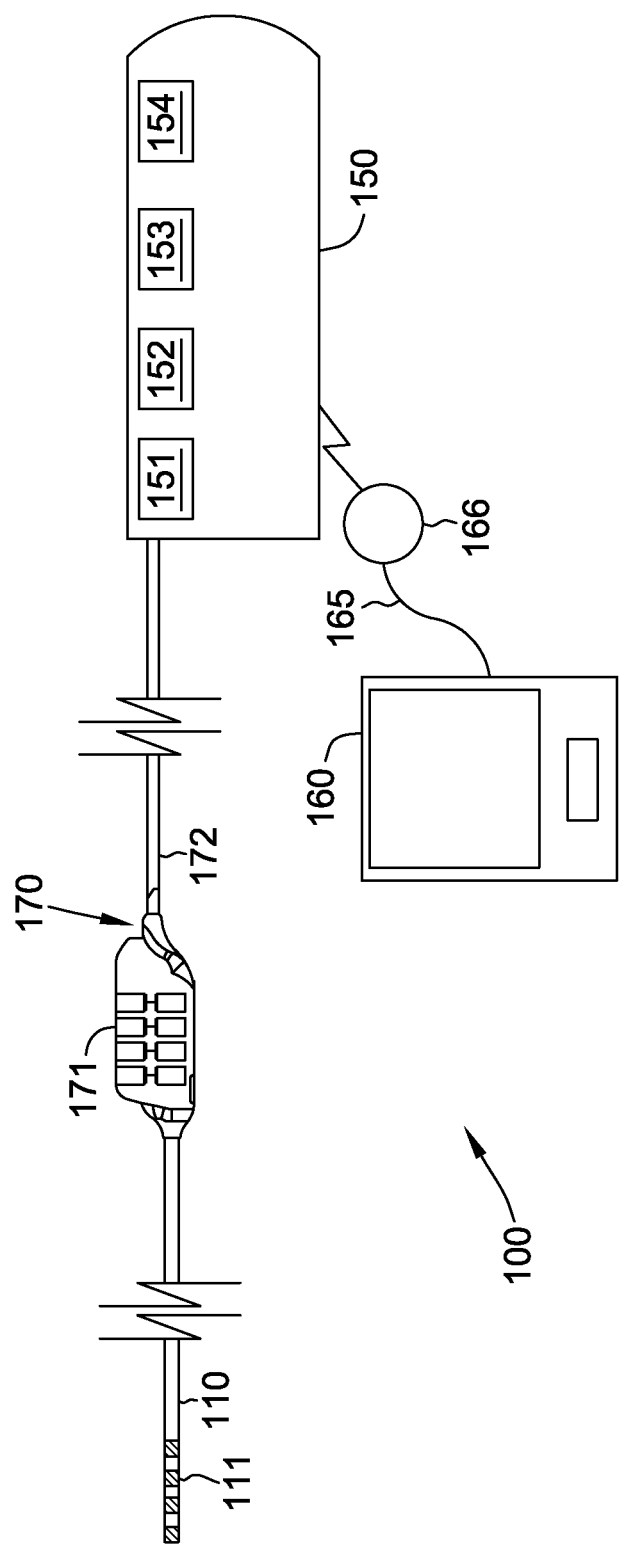
FIG. 1 is a schematic view of one embodiment of a stimulation system.

Referring now to the drawings, and in particular to FIG. 1, a stimulation system is indicated generally at 100. Stimulation system 100 generates electrical pulses for application to tissue of a patient, or subject, according to one embodiment. System 100 includes an implantable pulse generator (IPG) 150 that is adapted to generate electrical pulses for application to tissue of a patient. IPG 150 typically includes a metallic housing that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of IPG 150 for execution by the microcontroller or processor to control the various components of the device.

IPG 150 may comprise one or more attached extension components 170 or be connected to one or more separate extension components 170. Alternatively, one or more stimulation leads 110 may be connected directly to IPG 150. Within IPG 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from IPG 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171.

For implementation of the components within IPG 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within IPG 150. Different pulses on different electrodes may be generated using a single set of pulse generating circuitry using consecutively generated pulses according to a "multi-stim set program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number and type of electrodes 111, terminals, and internal conductors.

Controller device 160 may be implemented to recharge battery 153 of IPG 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller device 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery of IPG 150. The charging circuitry may also communicate status messages to controller device 160 during charging operations using pulse-loading or any other suitable technique. For example, controller device 160 may communicate the coupling status, charging status, charge completion status, etc.

External controller device 160 is also a device that permits the operations of IPG 150 to be controlled by user after IPG 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate IPG 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stim set during execution of program), etc. In the methods and systems described herein, parameters may include, for example, a number of pulses in a burst (e.g., 3, 4, or 5 pulses per burst), an intra-burst frequency (e.g., 130 Hz), an inter-burst frequency (e.g., 3-20 Hz), and a delay between a first and second burst.

IPG 150 modifies its internal parameters in response to the control signals from controller device 160 to vary the stimulation characteristics of stimulation pulses transmitted through stimulation lead 110 to the tissue of the patient. Neurostimulation systems, stim sets, and multi-stim set programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference. Example commercially available neurostimulation systems include the EON MINI™ pulse generator and RAPID PROGRAMMER™ device from Abbott Laboratories.

Beta band neuronal activity (e.g., activity in a frequency range from approximately 13-30 Hz) recorded using a DBS lead positioned in the basal ganglia may be used as a biomarker of PD. Further, beta band power in local field potential (LFP) recordings has been shown to strongly correlate with improved DBS contact selection.

Accordingly, the systems and methods described herein enable selecting DBS contacts based on analysis of LFP recordings. Notably, increased beta band activity and hypersynchrony of the basal ganglia causes more synchronized LFPs in the beta band. Accordingly, electrodes (i.e., contacts) on a DBS lead showing the highest connectivity to other electrodes on the DBS lead are a good candidate to select for use in DBS. Selecting such electrodes may improve therapeutic benefits and reduce abnormal beta band hypersynchrony.

In addition to facilitating optimal contact selection, analysis of LFPs can also be used as a biomarker in a closed loop control system in which the hypersynchrony of the basal ganglia can be continuously or intermittently monitored. Further, the selection of stimulation contacts can also be dynamically updated in real-time using analysis of LFPs, as described herein.

Figure 2:
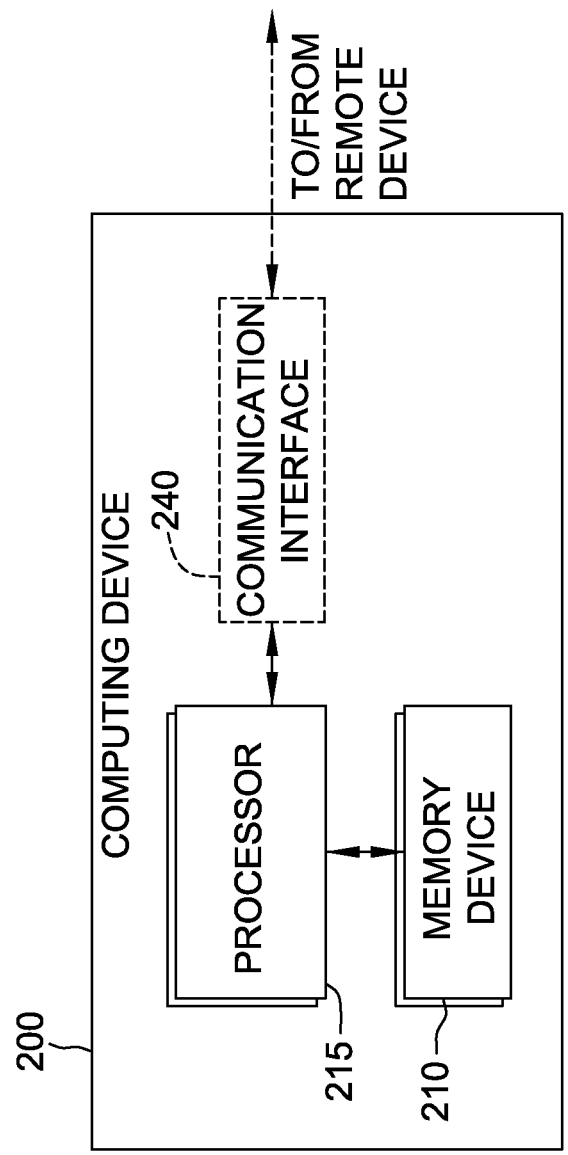
FIG. 2 is a block diagram of one embodiment of a computing device that may be used to select contacts for DBS.

FIG. 2 is a block diagram of one embodiment of a computing device 200 that may be used to select contacts based on analysis of LFP recordings, as described herein. Computing device 200 may be included, for example, within an IPG (e.g., IPG 150) or an external pulse generator.

In this embodiment, computing device 200 includes at least one memory device 210 and a processor 215 that is coupled to memory device 210 for executing instructions. In some embodiments, executable instructions are stored in memory device 210. In the illustrated embodiment, computing device 200 performs one or more operations described herein by programming processor 215. For example, processor 215 may be programmed by encoding an operation as one or more executable instructions and by providing the executable instructions in memory device 210.

Processor 215 may include one or more processing units (e.g., in a multi-core configuration). Further, processor 215 may be implemented using one or more heterogeneous processor systems in which a main processor is present with secondary processors on a single chip. In another illustrative example, processor 215 may be a symmetric multi-processor system containing multiple processors of the same type. Further, processor 215 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

In the illustrated embodiment, memory device 210 is one or more devices that enable information such as executable instructions and/or other data to be stored and retrieved. Memory device 210 may include one or more computer readable media, such as, without limitation, dynamic random access memory (DRAM), read-only memory (ROM), electrically erasable programmable read-only memory (EEPROM), static random access memory (SRAM), a solid state disk, and/or a hard disk. Memory device 210 may be configured to store, without limitation, application source code, application object code, source code portions of interest, object code portions of interest, configuration data, execution events and/or any other type of data.

Computing device 200, in the illustrated embodiment, includes a communication interface 240 coupled to processor 215. Communication interface 240 communicates with one or more remote devices, such as a clinician or patient programmer. To communicate with remote devices, communication interface 240 may include, for example, a wired network adapter, a wireless network adapter, a radio-frequency (RF) adapter, and/or a mobile telecommunications adapter.

Figure 3:
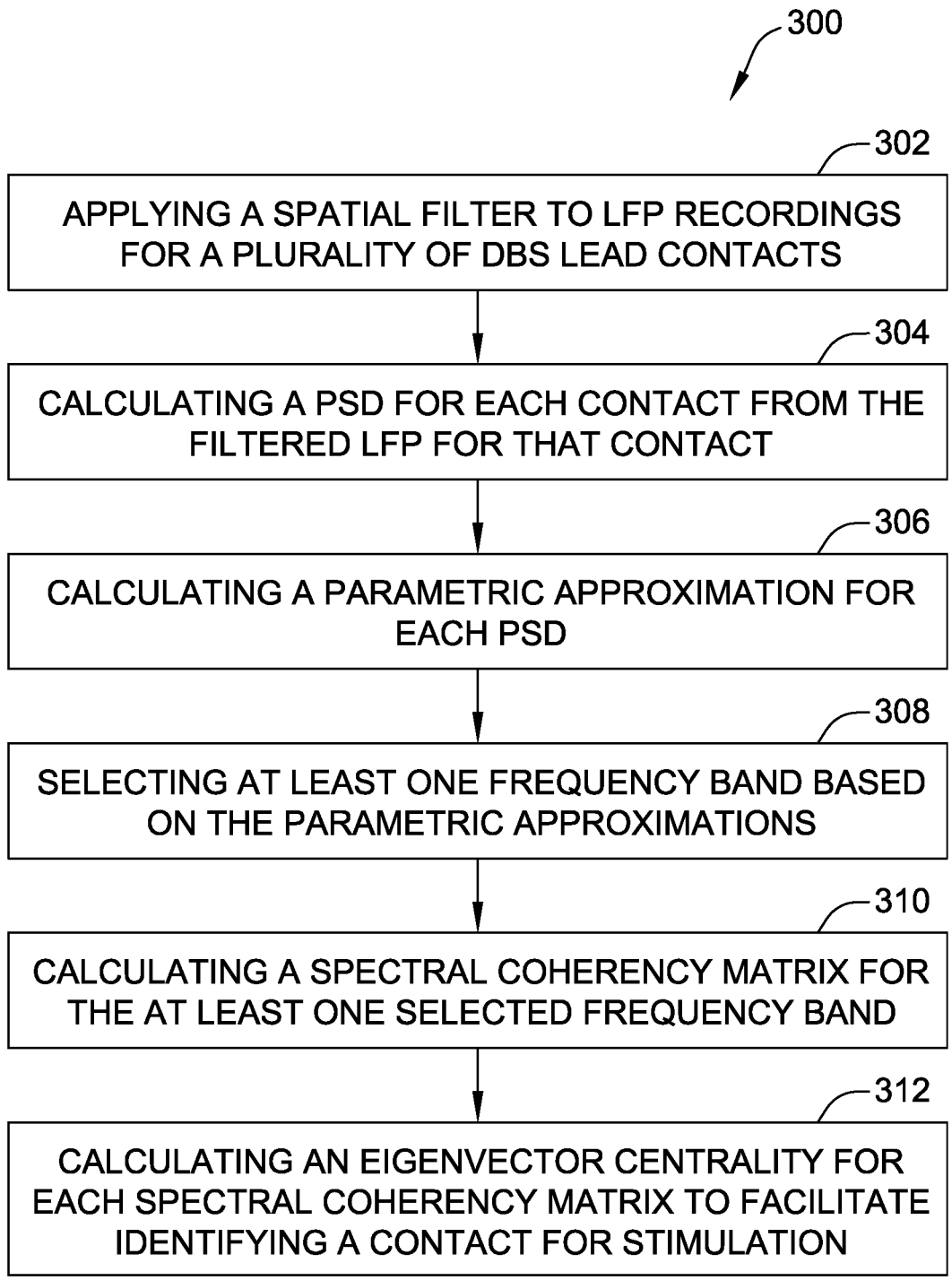
FIG. 3 is a flow diagram of a method of selecting contacts for DBS.

FIG. 3 is a flow diagram of a method 300 of selecting contacts for DBS. Method 300 may be implemented, for example, by computing device 200 (shown in FIG. 2). Method 300 includes applying 302 a spatial filter to LFP recordings acquired from a plurality of contacts on a DBS lead. The LFP recordings may be acquired, for example, during implantation of the DBS lead. Alternatively, the LFP recordings may be acquired after the DBS lead is already fully implanted (e.g., for use in a closed-loop control scheme, as described herein). Regardless, the LFP recordings are acquired during a time when stimulation is not being applied by the DBS lead.

The DBS lead may be any suitable stimulation lead including a plurality of contacts (also referred to herein as electrodes). In the exemplary embodiment, each contact is capable of functioning as both a stimulation electrode and a recording electrode (e.g., based on the signals received from a controller). For example, a first electrode may record electrical data in between application of stimulation pulses by that same electrode, while a second electrode may function as a dedicated recording electrode. In the exemplary embodiment, the LFP recordings are acquired for each contact simultaneously. Accordingly, if at least some of the plurality of contacts are being used to apply stimulation, the LFP recordings for each of the plurality of contacts are acquired at a particular time when no stimulation occurs by any of the contacts.

Figure 4:
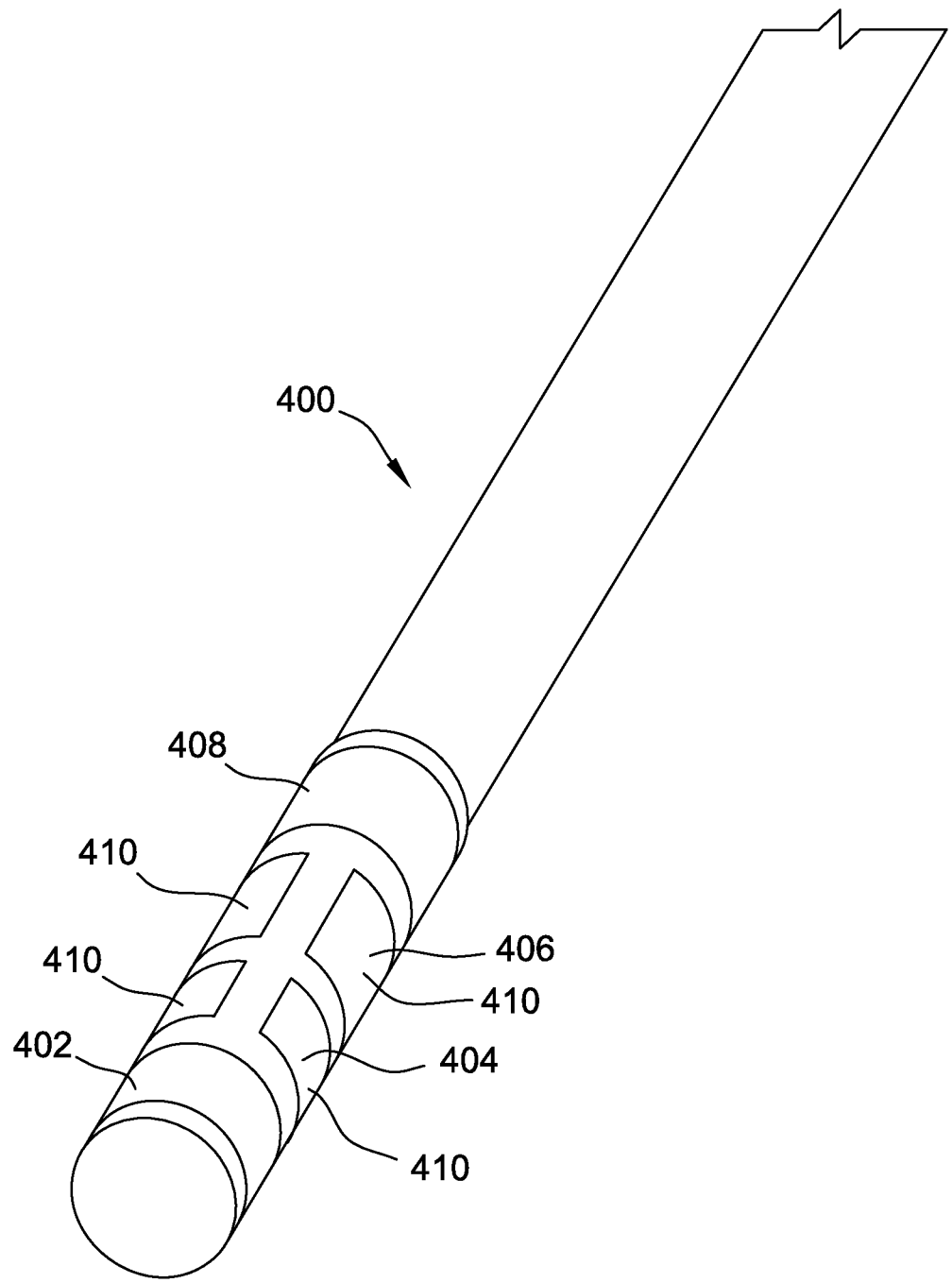
FIG. 4 is a perspective view of one embodiment of a DBS lead.

FIG. 4 is a perspective view of a DBS lead 400 that may be used to implement the systems and methods described herein. DBS lead 400 includes a first electrode 402, a second electrode 404, a third electrode 406, and a fourth electrode 408. In this embodiment, first electrode 402 and fourth electrode 408 are both ring electrodes. Further, second electrode 404 includes three segmented electrodes 410 (two of which are shown in FIG. 4), and third electrode 406 includes three segmented electrodes 410 (two of which are shown in FIG. 4). In the following figures, first electrode 402 is designated "1", the three segmented electrodes 410 of second electrode 404 are designated "2A-2C", the three segmented electrodes 410 of third electrode 406 are designated "3A-3C", and fourth electrode 408 is designated "4". Those of skill in the art will appreciate that DBS lead 400 may have any suitable electrode configuration, and that the electrode configuration shown in FIG. 4 is merely an example.

Referring back to FIG. 3, to apply 302 a spatial filter, a common average reference (CAR) filter or Laplacian filter may be applied 302. Applying 302 a spatial filter facilitates eliminating common signals such as artifacts and 60 Hz noise that affect the LFPs recorded at all contacts simultaneously. For example, to apply 302 a CAR filter, for each contact, the average LFP value for all the contacts is subtracted from the LFP value for that contact. For a Laplacian filter, for each contact, the average LFP value of only the adjacent contacts is subtracted from the LFP value for that contact. Alternatively, or additionally, spatial filters other than a CAR filter or a Laplacian filter may be used to enhance the signal to noise ratio of the LFPs.

Method 300 further includes calculating 304 a power spectral density (PSD) for each contact from the filtered LFP for each contact. The PSD may be calculated 304, for example, using Welch's method or a multitaper method. Alternatively, the PSD may be calculated 304 using any suitable method.

Figure 5A:
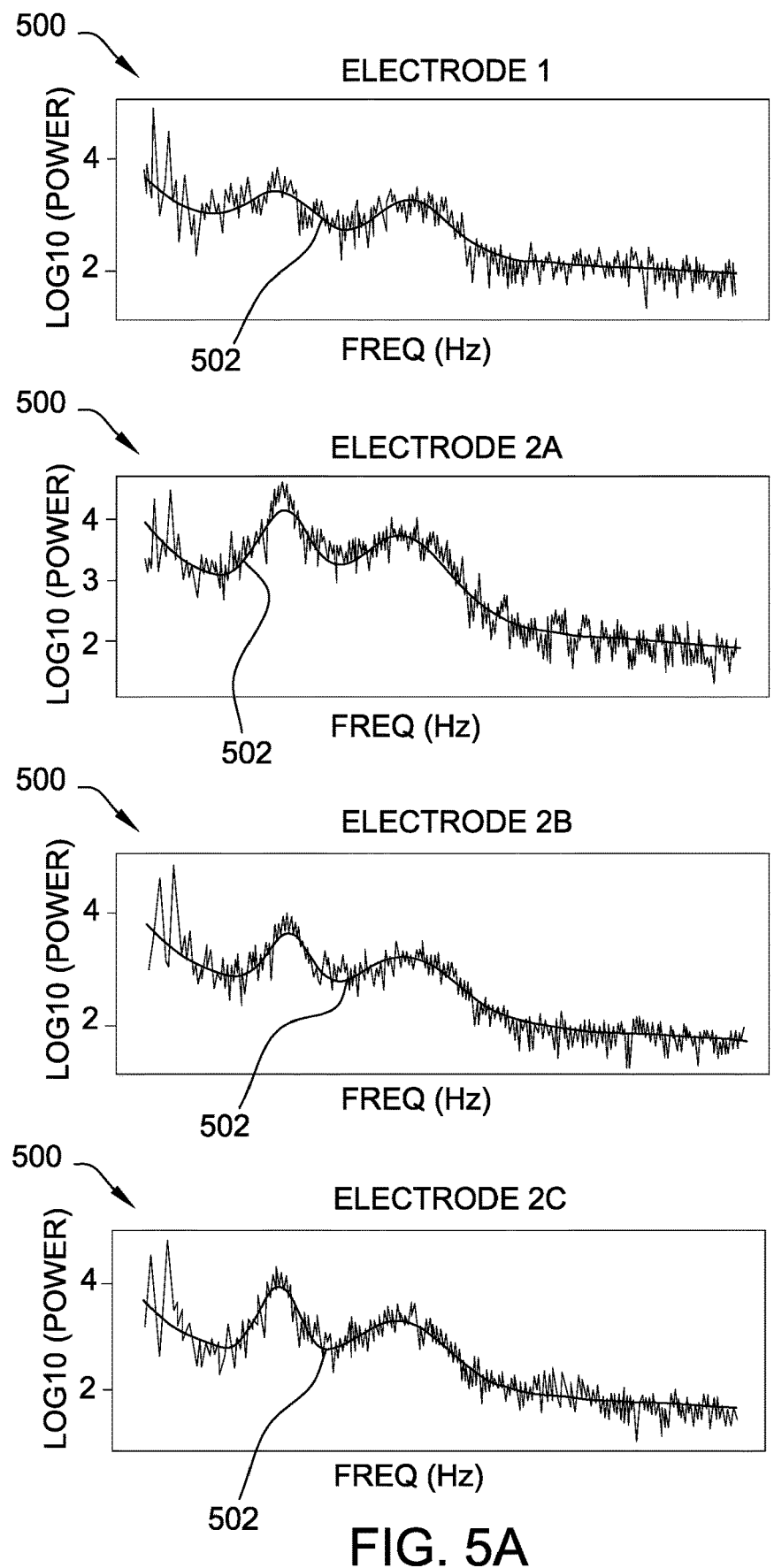
FIGS. 5A and 5B show a plurality of power spectral density (PSD) plots.
Figure 5B:
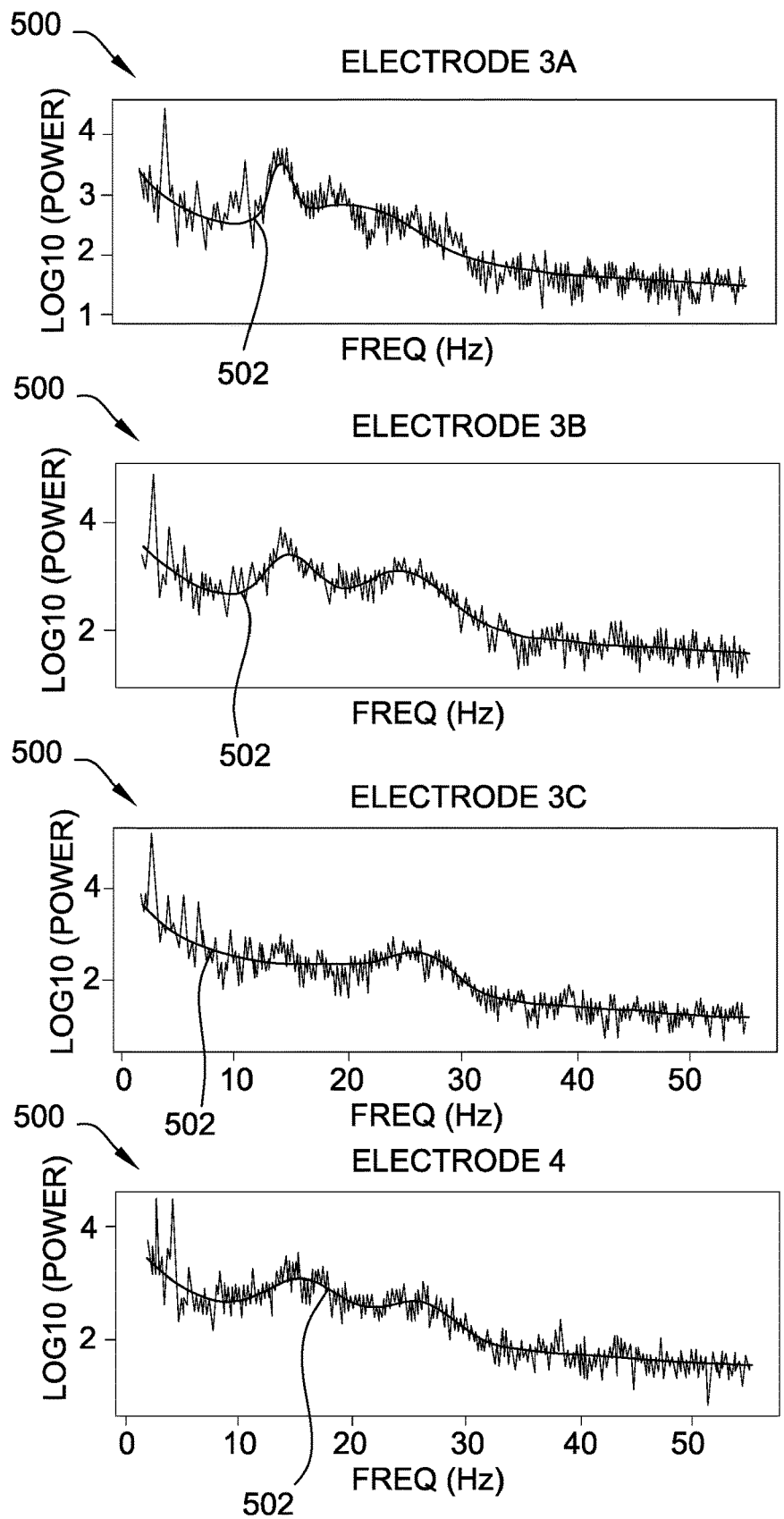

FIGS. 5A and 5B show a plurality of PSD plots 500. Specifically, plots 500 show an example PSD for each contact in DBS lead 400 (shown in FIG. 4). Specifically, a PSD is shown for first electrode 402, the three segmented electrodes 410 of second electrode 404, the three segmented electrodes of third electrode 406, and fourth electrode 408.

Method 300 further includes calculating 306 a parametric approximation for each PSD. In FIGS. 5A and 5B, each plot 500 includes a parametric approximation 502 of the PSD for that contact. Parametric approximation 502 may be calculated 306, for example using Gaussian mixtures and an aperiodic log-linear function. Further, those of skill in the art will appreciate that other parametric approximation techniques may be used. Parametric approximation 502 of the PSD will generally delineate individual specific pathological oscillatory frequency bands.

As noted above, movement disorders (e.g., PD, ET, and dystonia) may be characterized by abnormal oscillatory brain activity, including higher than normal frequency oscillation in the beta band. Because the particular oscillatory frequency bands are generally patient-specific, in the example embodiment, method 300 further includes selecting 308 at least one frequency band based on the parametric approximations 502. More specifically, in the exemplary embodiment, to select 308 at least one frequency band, method 300 includes attempting to estimate at least one oscillatory frequency band based on the parametric approximations 502 calculated for each contact. That is, the pathological oscillatory frequency bands may be estimated using parametric approximation 502 of the PSD. An oscillatory frequency band in the PSD plot will have a higher power compared to neighboring frequencies. Further, the PSD at the oscillatory frequency band can be approximated with a Gaussian function.

However, it some circumstances, it may be difficult to estimate at least one oscillatory frequency band for a patient. Accordingly, when estimation fails, to select 308 at least one frequency band, method 300 includes selecting the beta frequency band (e.g., approximately 13-30 Hz).

Subsequently, method 300 includes calculating 310 a spectral coherency matrix that includes the spectral coherence between each pair of contacts within the at least one selected frequency band. That is, a spectral coherency matrix is calculated 310 for each of the at least one oscillatory frequency bands (when able to be estimated) or the beta frequency band (when the oscillatory frequency bands are not able to be estimated). The spectral coherence between a pair of given contacts represents how well the LFPs for those contacts correlate in the frequency domain.

Figure 6:
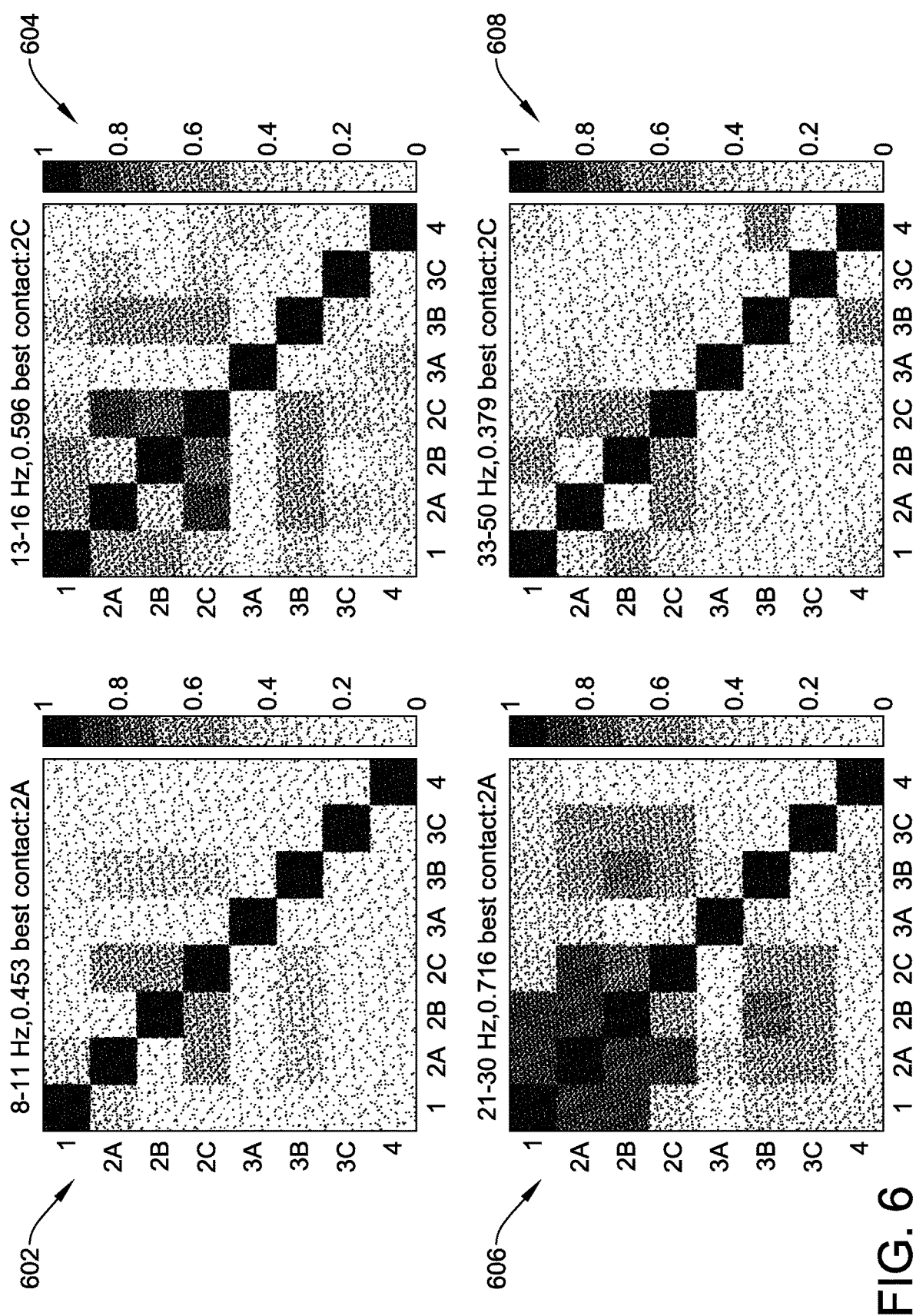
FIG. 6 is a plurality of spectral coherency matrices.

FIG. 6 shows a plurality of spectral coherency matrices. Specifically, FIG. 6 includes a first matrix 602 for a frequency range of 8-11 Hz, a second matrix 604 for a frequency range of 13-16 Hz, a third matrix 606 for a frequency range of 21-30 Hz (i.e., corresponding to the high beta band), and a fourth matrix 608 for a frequency range of 33-50 Hz.

Each matrix 602, 604, 606, 608 includes a plurality of cells, with each cell showing the spectral coherence between two contacts (e.g., two of first electrode 402, the three segmented electrodes 410 of second electrode 404, the three segmented electrodes 410 of third electrode 406, and fourth electrode 408 as shown in FIG. 4).

Referring back to FIG. 3, method 300 further includes calculating 312 an eigenvector centrality for each spectral coherence matrix. The eigenvector centrality is calculated 312 such that the largest eigenvalue is a centrality score indicating the degree of synchronization (i.e., how well the LFPs for the contacts correlate in the frequency domain) in the associated frequency band.

Eigenvector centrality is a measure of the influence of a node in a network. In LFP recordings with DBS leads, eigenvector centrality measures the influence of the neuronal oscillatory activity of a population of neurons near each contact to the neuronal activity of other population of neurons measured at other contacts. The element in the corresponding eigenvector accounts for the contribution of each contact to the eigenvector centrality. That is, the contact with the highest value contributes the most to the centrality (and thus, has the highest synchronization with the other contacts). On the other hand, contacts with lower values contribute less to the centrality. In the embodiments described herein, the eigenvector centrality is calculated using eigen-decomposition of the coherence matrix, and the eigenvector corresponding to the largest eigenvalue is used to find the most influencing contact. As shown in FIG. 6, third matrix 606 (corresponding to the high beta band) demonstrates the highest centrality relative to the other matrices 602, 604, and 608. Further, for third matrix 606, electrode 2A has the highest value.

Based on the calculated 312 eigenvector centrality, certain contacts may be selected to apply stimulation during a DBS programming session. In one embodiment, during the DBS programming session, controller device 160 may display one or more suggested contacts to enable the clinician to select those contacts for use in stimulation. For example, controller device 160 may display the contact with the highest value in the eigenvector centrality, and the clinician, upon observing the display, may initially select that contact to apply stimulation. If, based on testing, that contact is deemed undesirable for stimulation (e.g., due to inefficacy, side effects, etc.), the next contact with the next highest value may be selected by the clinician to apply stimulation.

The eigenvector centrality can also be used in other applications. For example, in some embodiments, IPG 150 (shown in FIG. 1) may implement method 300 in a closed-loop control scheme to dynamically update DBS applied using system 100. Specifically, IPG 150 may periodically perform the steps of method 300 to determine which contact has the highest value currently, and automatically apply stimulation using that contact.

As another example, the eigenvector centrality may be used to determine whether or not to apply stimulation to a patient. In one embodiment, IPG 150 periodically performs the steps of method 300, and only applies stimulation when a maximum eigenvalue of the coherence matrix is above a predetermined threshold (e.g., indicating hypersynchrony). Selectively activating stimulation based on the eigenvector centrality may, for example, improve battery life of IPG 150.

The embodiments described herein provide systems and methods for selecting contacts for use in deep brain stimulation (DBS). A spatial filter is applied to local field potential (LFP) recordings for a plurality of contacts of a DBS lead, and a power spectral density (PSD) is calculated for each contact from the filtered LFP for that contact. Further, a parametric approximation for each PSD is calculated, and at least one frequency band is selected based on the parametric approximations. For each of the at least one selected frequency band, a spectral coherency matrix is calculated, and an eigenvector centrality is calculated for each spectral coherency matrix to facilitate identifying a contact for stimulation.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A computing device for selecting contacts for use in deep brain stimulation (DBS), the computing device comprising:
   a processor; and
   a memory device communicatively coupled to the processor, the memory device including instructions that, when executed, cause the processor to:
      apply a spatial filter to local field potential (LFP) recordings for a plurality of contacts of a DBS lead;
      calculate a power spectral density (PSD) for each contact from the filtered LFP for that contact;
      calculate a parametric approximation for each PSD;
      select at least one frequency band based on the parametric approximations;
      calculate a spectral coherency matrix for each of the at least one selected frequency band; and
      calculate an eigenvector centrality for each spectral coherency matrix to facilitate identifying a contact for stimulation.

2. The computing device of claim 1, wherein the instructions further cause the processor to display the contact that has the highest value in the eigenvector centrality.

3. The computing device of claim 1, wherein the instructions further cause the processor to automatically select the contact having the highest value in the eigenvector centrality for stimulation.

4. The computing device of claim 1, wherein to apply a spatial filter, the instructions further cause the processor to apply one of a common average reference filter and a Laplacian filter.

5. The computing device of claim 1, wherein the at least one selected frequency band is within a range from approximately 13 to 30 Hertz.

6. The computing device of claim 1, wherein to select at least one frequency band, the instructions cause the processor to estimate at least one oscillatory frequency band based on the parametric approximations.

7. The computing device of claim 1, wherein to select at least one frequency band, the instructions cause the processor to select the beta frequency band.

8. A computer-implemented method for selecting contacts for use in deep brain stimulation (DBS), the method comprising:
   applying a spatial filter to local field potential (LFP) recordings for a plurality of contacts of a DBS lead;
   calculating a power spectral density (PSD) for each contact from the filtered LFP for that contact;
   calculating a parametric approximation for each PSD;

selecting at least one frequency band based on the parametric approximations;

calculating a spectral coherency matrix for each of the at least one selected frequency band; and calculating an eigenvector centrality for each spectral coherency matrix to facilitate identifying a contact for stimulation.

9. The method of claim 8, further comprising displaying the contact that has the highest value in the eigenvector centrality.

10. The method of claim 8, further comprising automatically selecting the contact having the highest value in the eigenvector centrality for stimulation.

11. The method of claim 8, wherein applying a spatial filter comprises applying one of a common average reference filter and a Laplacian filter.

12. The method of claim 8, wherein the at least one selected frequency band is within a range from approximately 13 to 30 Hertz.

13. The method of claim 8, wherein the at least one selected frequency band includes a plurality of frequency bands.

14. The method of claim 8, wherein the plurality of contacts include a first ring electrode, a second ring electrode, a first segmented electrode, and a second segmented electrode.

15. A system for deep brain stimulation (DBS), the system comprising:

a DBS lead comprising a plurality of contacts; and a computing device communicatively coupled to the DBS lead, the computing device configured to:

apply a spatial filter to local field potential (LFP) recordings for the plurality of contacts;

calculate a power spectral density (PSD) for each contact from the filtered LFP for that contact;

calculate a parametric approximation for each PSD;

select at least one frequency band based on the parametric approximations;

calculate a spectral coherency matrix for each of the at least one selected frequency band; and calculate an eigenvector centrality for each spectral coherency matrix to facilitate identifying a contact for stimulation.

16. The system of claim 15, wherein the computing device is further configured to display the contact that has the highest value in the eigenvector centrality.

17. The system of claim 15, wherein the computing device is further configured to automatically select the contact having the highest value in the eigenvector centrality for stimulation.

18. The system of claim 15, wherein the at least one selected frequency band is within a range from approximately 13 to 30 Hertz.

19. The system of claim 15, wherein the at least one selected frequency band includes a plurality of frequency bands.

20. The system of claim 15, wherein the plurality of contacts comprises a first ring electrode, a second ring electrode, a first segmented electrode, and a second segmented electrode.

* * * * *